United States Patent
Giese et al.

(10) Patent No.: US 10,493,379 B2
(45) Date of Patent: Dec. 3, 2019

(54) CAGED BAGS OF POROUS MATERIALS

(71) Applicants: Roger W. Giese, Hanover, MA (US); Zhenwei Shi, West Roxbury, MA (US); Michael R. MacNeil, Quincy, MA (US); Poguang Wang, Westborough, MA (US)

(72) Inventors: Roger W. Giese, Hanover, MA (US); Gang Shao, West Roxbury, MA (US); Michael R. MacNeil, Quincy, MA (US); Poguang Wang, Westborough, MA (US)

( * ) Notice: Subject to any disclaimer, the term of this patent is extended or adjusted under 35 U.S.C. 154(b) by 0 days.

(21) Appl. No.: 13/955,512

(22) Filed: Jul. 31, 2013

(65) Prior Publication Data
US 2013/0313198 A1    Nov. 28, 2013

Related U.S. Application Data

(63) Continuation of application No. PCT/US2012/023813, filed on Feb. 3, 2012.
(Continued)

(51) Int. Cl.
| | |
|---|---|
| *B01D 15/20* | (2006.01) |
| *B01D 15/18* | (2006.01) |
| *B01D 15/12* | (2006.01) |
| *B01J 8/00* | (2006.01) |
| *B01J 8/02* | (2006.01) |
| *B01J 19/24* | (2006.01) |
| *B01J 20/00* | (2006.01) |

(Continued)

(52) U.S. Cl.
CPC ......... *B01D 15/1892* (2013.01); *B01D 15/12* (2013.01); *B01D 15/20* (2013.01); *B01J 8/008* (2013.01); *B01J 8/02* (2013.01); *B01J 19/2485* (2013.01); *B01J 20/00* (2013.01); *B01J 20/103* (2013.01); *B01J 20/20* (2013.01); *B01J 20/261* (2013.01); *B01J 20/2805* (2013.01); *G01N 1/405* (2013.01); *G01N 30/14* (2013.01); *B01J 2208/00876* (2013.01); *B01J 2208/00884* (2013.01); *B01J 2208/028* (2013.01); *B01J 2219/2449* (2013.01); *B01J 2219/2498* (2013.01); *G01N 2030/009* (2013.01)

(58) Field of Classification Search
CPC .... B01D 15/1892; B01D 15/12; B01D 15/20; B01J 20/103; B01J 20/20; B01J 20/261; B01J 20/2805; B01J 20/00; B01J 19/2485; B01J 8/02; B01J 8/008; G01N 1/405; G01N 30/14
USPC ........ 210/615–617, 619, 660, 282, 283, 289
See application file for complete search history.

(56) References Cited

U.S. PATENT DOCUMENTS

| | | | | |
|---|---|---|---|---|
| 2,316,353 | A | * | 4/1943 | Moorhead ............. A47L 9/1427 15/DIG. 8 |
| 4,005,010 | A | * | 1/1977 | Lunt ............................. 210/615 |

(Continued)

OTHER PUBLICATIONS

International Search Report and Written Opinion issued by the U.S. Patent and Trademark Office as International Searching Authority for International Application No. PCT/US2012/023813 dated May 23, 2012 (10 pages).

*Primary Examiner* — Chester T Barry
(74) *Attorney, Agent, or Firm* — Lawrence P. Zale; Zale Patent Law, Inc.

(57) ABSTRACT

Systems and methods employing beds of bagged and caged absorbent and adsorbent materials are disclosed. These inventions are useful in the area of solid phase extraction.

21 Claims, 6 Drawing Sheets

Related U.S. Application Data

(60) Provisional application No. 61/439,131, filed on Feb. 3, 2011.

(51) Int. Cl.

| | | |
|---|---|---|
| *G01N 1/40* | (2006.01) | |
| *G01N 30/14* | (2006.01) | |
| *B01J 20/28* | (2006.01) | |
| *B01J 20/20* | (2006.01) | |
| *B01J 20/26* | (2006.01) | |
| *B01J 20/10* | (2006.01) | |
| *G01N 30/00* | (2006.01) | |

(56) References Cited

U.S. PATENT DOCUMENTS

| | | | | |
|---|---|---|---|---|
| 4,099,619 A | * | 7/1978 | Hudler | E02B 15/06 206/524.1 |
| 4,366,067 A | * | 12/1982 | Golding | C02F 1/681 210/242.4 |
| 4,511,461 A | | 4/1985 | Kruyer | |
| 4,793,837 A | * | 12/1988 | Pontius | B01D 53/02 427/244 |
| 5,423,985 A | * | 6/1995 | Addeo | C02F 1/681 210/242.4 |
| 5,700,375 A | * | 12/1997 | Hagen | B01D 39/1623 210/500.1 |
| 5,891,559 A | | 4/1999 | Goken et al. | |
| 5,911,883 A | | 6/1999 | Anderson | |
| RE36,811 E | | 8/2000 | Markell et al. | |
| 6,277,280 B1 | * | 8/2001 | Houck | 210/616 |
| 6,492,183 B1 | | 12/2002 | Perman et al. | |
| 6,843,909 B1 | * | 1/2005 | Woltmann | A01K 63/045 119/260 |
| 7,381,333 B1 | * | 6/2008 | Rainer | C02F 1/286 210/660 |
| 2003/0015467 A1 | * | 1/2003 | Johnston et al. | 210/502.1 |
| 2003/0033755 A1 | * | 2/2003 | Lord | 52/3 |
| 2003/0141259 A1 | * | 7/2003 | Madrid | C02F 1/004 210/602 |
| 2007/0130894 A1 | * | 6/2007 | Schultink | A47L 9/14 55/381 |
| 2007/0299149 A1 | * | 12/2007 | Goldshtein | B01J 20/22 521/41 |
| 2009/0075075 A1 | * | 3/2009 | Abrams | D06P 5/004 428/354 |
| 2010/0316832 A1 | * | 12/2010 | Abrams | D06Q 1/12 428/90 |
| 2011/0126644 A1 | * | 6/2011 | Hayes | G01N 1/10 73/863.23 |
| 2011/0309023 A1 | * | 12/2011 | Kane et al. | 210/681 |
| 2012/0145640 A1 | * | 6/2012 | Davis et al. | 210/688 |

\* cited by examiner

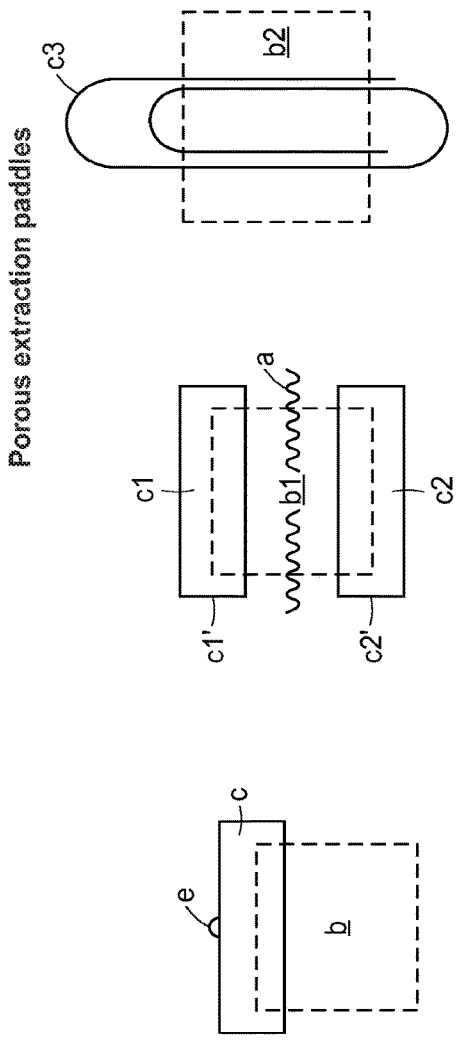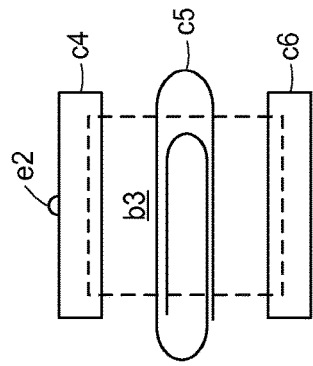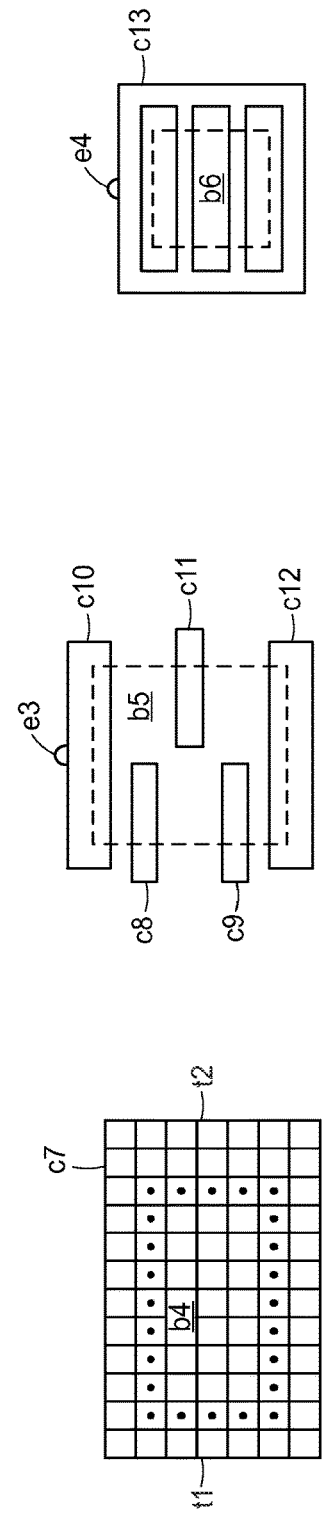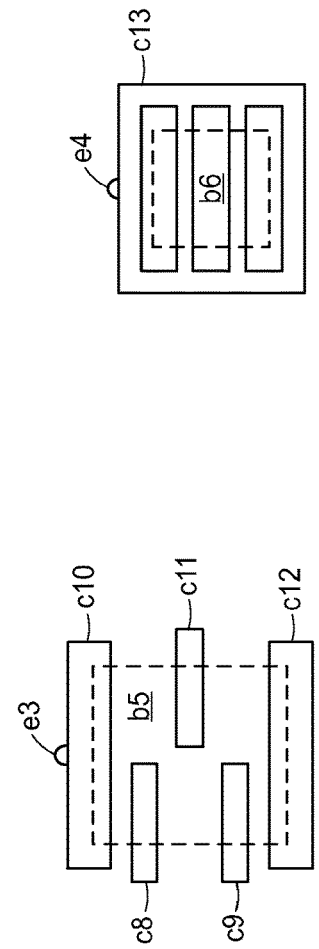

side view top view

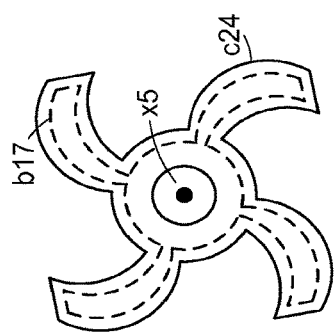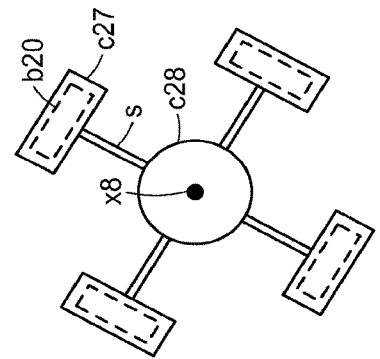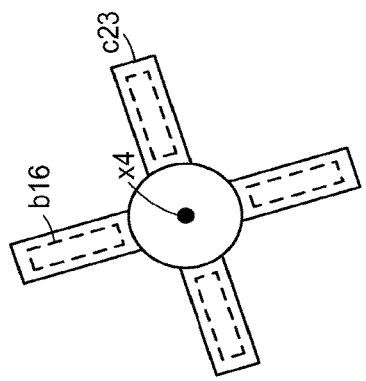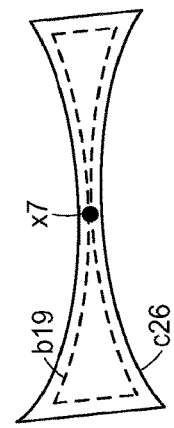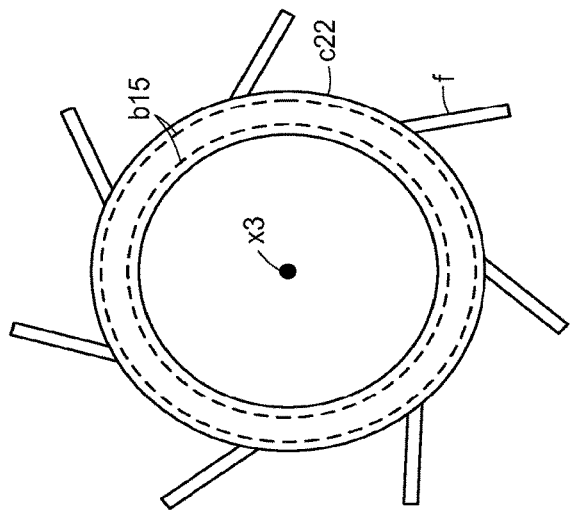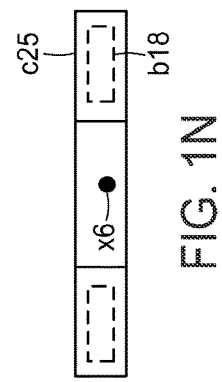

Motor-connected porous extraction paddle in a jar.

Motor-connected porous extraction paddle.

Bagged beds of porous materials caged in containers.

CAGED BAGS OF POROUS MATERIALS

CROSS REFERENCE TO RELATED APPLICATIONS

This application is a Continuation of International Application No. PCT/US12/23813, filed Feb. 3, 2012, entitled CAGED BAGS OF POROUS MATERIALS, which claims the benefit of U.S. Provisional Application No. 61/439,131, filed Feb. 3, 2011, entitled POROUS EXTRACTION PADDLE, the entire contents of both are incorporated by reference herein.

STATEMENT REGARDING FEDERALLY SPONSORED RESEARCH OR DEVELOPMENT

This invention was supported in part by National Institute of Environmental Health Sciences grant 5 P42 ES017198-02.

FIELD OF THE INVENTION

The invention is generally directed to methods and systems for solid phase extraction. More specifically, the invention is related to novel methods and systems for adsorption and absorption of chemical and biological substance of interest out of mixtures.

BACKGROUND OF THE INVENTION

Targeted chemical analysis of dilute samples can be expensive difficult with current methods and systems. For example, if small amounts of an analyte are present in a sample, it is desirable to remove the analyte from the sample or concentrate the analyte in order to detect its presence. These constraints can make it difficult in situations were large volume samples must be shipped and processed in order to be used.

Similar issues exist when a sample has a small volume. Sample must be conserved in order to be able to run tests in duplicate. Simply diluting small volume samples to obtain a greater volume for testing is not feasible where the analyte of interest exists in low concentrations.

Solid phase extraction is a widely employed method for isolating chemical and biological substances of interest out of mixtures by adsorption or absorption. Solid phase extraction in modern chemical analysis is most commonly conducted in a column mode where the sample is flowed through an immobilized zone of porous adsorbent material by gravity, pumping or vacuum. However, accessory equipment is required to use the columns, columns clog when insolubles are present in the samples, columns are expensive (especially large columns to extract larger samples), and columns can vary in their performance because of variation in how well they are packed.

It is difficult to avoid using columns when using chromatographic extraction particles because without the protection of the column apparatus, many chromatographic extraction particles readily fragment by abrasion to small particulates (fines) when a bag of them is handled or tumbled. This would contaminate the scientist and sample with fines that migrate out of the bag. Reproducibility is compromised and sample is lost.

Analysts often desire the ability to extract multiple analytes simultaneously by solid phase extraction. However, no single adsorbent column gives a good recovery for all of the analytes. While multiple columns may be used, this is expensive, as well as time and space consuming. It also not feasible to prepare a single column with multiple adsorbents since column preparation requires special hardware and many adsorbants particles are of different sizes which can lead to impeding the flow of sample through a column.

Solid phase microextraction (SPME) techniques can be used to extract small sample volumes. In SPME, the outside of a solid fused silica fiber, or the inside of a fused silica capillary tubing, is coated, covalently or noncovalently, with an organic polymer. However, the fibers are expensive, difficult to make, and fragile. Thinner fiber coatings reduce sensitivity and thicker coatings reduce analysis speed. Relatively few coatings are available since ease of fabrication is coating-dependent.

Expanded bed liquid chromatography is a technique for preparative isolation of analytes in large, usually industrial-level, liquid samples having interfering insolubles. The upward flow of the sample through a loose bed of the chromatographic particles achieves solid phase extraction. Unfortunately, it is difficult to set up and maintain conditions which achieve efficient extraction of analytes in a relatively short time, while also removing all of the undesired insolubles. If the flow rate is too fast, the extraction efficiency is lower and the chromatographic reagent particles are lost with the sample insolubles by the upwards solvent flow. If the flow rate is slow, sample insolubles are not removed enough, and the process becomes too slow to be cost effective.

Thus, there is a need for systems and methods of solid phase extraction that can be used to extract single or multiple analytes in a relatively short time from samples of a wide variety of matrices and of dilute and/or small volume.

SUMMARY OF THE INVENTION

According to aspects of the present disclosure, methods and systems are disclosed to overcome the limitations of known techniques and systems based on beds of porous materials such as adsorbents for solid phase extractions. The systems and methods disclosed herein utilize a bed configuration stabilized first by a porous bag, and then by a cage. In some embodiments the cage is part of the bag, in others, the cage is external to the bag, and in yet others the cage is inside the bag. The cage advances the preparation, properties and performance of the bed in several ways that overcome or minimize the problems of prior systems and methods in a number of ways, including cost, speed, efficiency, reproducibility, ruggedness and formation of fines.

In particular embodiments, a bagged, caged bed of porous adsorbent material is affixed to a motor to create a "paddle" configuration. The paddle can be used to stir a larger sample, thereby performing a solid phase extraction of the sample. In other embodiments, solid phase extraction of a sample can be performed by placing a caged bagged bed of porous adsorbent material in a small container that contains the sample of interest. The container may also be shaken or agitated in some manner to enhance the speed or amount of adsorption of the analyte of interest.

Embodiments described herein relate generally to a caged porous bag comprising a bed of solid phase material within a porous meshed cloth bag, at least a first part of the bag being locked in a cage, wherein the bed has a minimum width that is defined as the minimum distance through the bed along a straight line that intersects at least one porous meshed side of the bed at a right angle and passes through a point at the center of mass of the bed, said straight line passing sequentially through a porous meshed side of the bag, the bed, and a second porous meshed side of the bag with said sides of the bag contacting the bed where said line passes through, and wherein the bed has a maximum length which is the distance between the two ends of the bed that are farthest apart, and the ratio of said length to the said width is at least 2. In some embodiments, the ratio of said length to said width of the bed is at least 5. In other embodiments, the ratio of said length to said width of the bed is at least 10.

In some embodiments, at least 90% of the volume of the meshed cloth bag is occupied by the bed. In other embodiments, at least part of the bed is immobilized in the meshed cloth bag by the cage. In further embodiments, at least one part of the meshed cloth bag is locked in contact with the cage by mechanical stress. In yet other embodiments, at least one part of the meshed cloth bag is locked into contact with the cage by embedding or covalent binding. In still further embodiments, at least one porous part of the meshed cloth bag is locked in contact with a cage. In some embodiments, the cage is external to the meshed cloth bag. In other embodiments, the cage comprises a container, wherein at least part of the cage is in contact with the inside wall of the container.

In some embodiments, the porous parts of the meshed cloth bag are uniformly porous. In still other embodiments, the pores in the porous meshed cloth are selected from the range of about 1 to about 100 microns. In yet other embodiments, the meshed cloth bag comprises woven cloth. In some embodiments, the cloth comprises woven porous polyamide (such as nylon), polyester, polyalkyl (such as polypropylene) or metal. In some embodiments, the cage comprises one or more rigid or semi-rigid meshes. In still others, the cage comprises a metal, glass or plastic. In further embodiments, the cage is connected to a motor. In still further embodiments at least one component of the cage comprises a mesh, bar, rod, stick, magnet, wire, spring, cable tie, tie wrap, tagging fastener or barb, clamp, frame, brace, clip, hook, cover, cap, lid, ring, a container, or equivalents thereof. In still further embodiments, at least one component of the cage comprises of a container. In yet other embodiments, the cage closes an opening of the meshed cloth bag.

In some embodiments of the invention, the solid phase material comprises a porous monolith, porous disc, porous membrane or porous filter. In others, at least some of the solid phase material comprises porous or nonporous particles. In yet others, the particles comprise biological cells. In still others, the particles comprise organic-bonded porous silica particles. In some embodiments, the size of greater than 50% of the particles have a diameter within the range of 5 µm to 100 µm. In others, the solid phase material is synthetic. In certain embodiments, the solid phase material is selected from the group consisting of graphitized carbon, graphitic carbon, charcoal carbon and graphitic, porous solids. In other embodiments, the solid phase material is coated with a substance that binds to a target analyte.

In further embodiments, the bag comprises a polyamide, polyester, polyalkyl, metal or polysaccharide. In still further embodiments, the cage comprises a metal. In yet further embodiments, the cage comprises a mesh, bar, rod, stick, magnet, wire, spring, cable tie, tie wrap, tagging fastener or barb, clamp, frame, brace, clip, hook, cover, cap, lid, ring, a container, or equivalents thereof.

Other embodiments described herein relate generally to a method of solid phase extraction comprising providing a caged porous bag comprising a bed of solid phase material within a porous meshed cloth bag, at least one part of the bag being locked in a cage, wherein the bed has a minimum width which is the minimum distance through the bed along a straight line that intersects at least one porous meshed side of the bed at a right angle and passes through a point at the center of mass of the bed, said straight line passing sequentially through a porous meshed side of the bag, the bed, and a second porous meshed side of the bag with said sides of the bag contacting the bed where said line passes through, and wherein the bed has a maximum length which is the distance between the two ends of the bed that are farthest apart, and the ratio of said length to the said width is at least 2; providing a container containing a liquid comprising dissolved or undissolved substances of interest; inserting said caged porous bag into said container containing a liquid; moving said caged porous bag through said liquid; and extracting said dissolved or undissolved substances of interest. In some embodiments, the moving of the caged bag is accomplished by shaking or rotating.

Some embodiments described herein relate generally to a method of solid phase extraction comprising providing a caged porous bag comprising a bed of solid phase material within a porous meshed cloth bag, at least one part of the bag being locked in contact with a cage, wherein the bed has a minimum width which is the minimum distance through the bed along a straight line that intersects at least one porous meshed side of the bed at a right angle and also passes through a point at the center of mass of the bed, said straight line passing sequentially through a porous meshed side of the bag, the bed, and a second porous meshed side of the bag with said sides of the bag contacting the bed where said line passes through, and wherein the bed has a maximum length which is the distance between the two ends of the bed that are farthest apart, and the ratio of said length to the said width is at least 2; providing a container filled with a liquid comprising dissolved or undissolved substances of interest; inserting said caged porous bag into said container filled with a liquid; moving said liquid in said container while said caged porous bag remains stationary in the container; and extracting said dissolved or undissolved substances of interest. In some embodiments, the moving of said liquid is accomplished by stirring, rotating, shaking or pumping. In other embodiments, the substance of interest is an analyte.

Still other embodiments of the invention described herein relate generally to a roll of uniformly porous mesh tubing that is heat sealed along its side edges, suitable for use as a caged porous bag. In some embodiments, the pore size is selected from the range of 1 to 100 microns.

Still other embodiments of the invention described herein relate generally to an oblong, porous meshed flattened bag having a first end and a second end, wherein the first end is sealed, the minimal internal distance from the second end to the first end defines the length, wherein the ratio of the length to the maximum internal width of the bag is at least 1.5, where the width is measured perpendicular to the length. In some embodiments, the ratio is at least 3. In other embodiments, the width is less than about 10 mm. In yet further embodiments, the width is less than about 5 mm.

In further embodiments of the invention the bag comprises polyamide, polyester, polyalkyl, or metal. In still other embodiments, the pores of the bag are from about 1 to about 100 microns. In other embodiments, at least one part of the bag is locked in contact with a cage, and the bag contains a bed of porous material. In yet other embodiments, at least one porous part of the bag is locked in contact with a cage. In still other embodiments, the porous material is synthetic. In still further embodiments, the porous material comprises porous organic-bonded silica particles or biological cells.

In some embodiments, the cage comprises a mesh, bar, rod, stick, magnet, wire, spring, cable tie, tie wrap, tagging fastener or barb, clamp, frame, brace, clip, hook, cover, cap, lid, ring, a container, or equivalents thereof. In still others, the cage comprises a container. In further embodiments, the volume of the container is less than 5 ml. In still further embodiments, the first end of a bag is the bottom of the bag as defined by the orientation of the bag to a cage when the bag is attached to the cage. In even further embodiments, the second end is the top of the bag as defined by the orientation of the bag to a cage when the bag is attached to the cage. In yet further embodiments, at least two sides of the bag are heat sealed.

DESCRIPTION OF THE FIGURES

The following figures are presented for the purpose of illustration only, and are not intended to be limiting.

DETAILED DESCRIPTION OF THE INVENTION

1. Definitions

Figures 1, 1H:
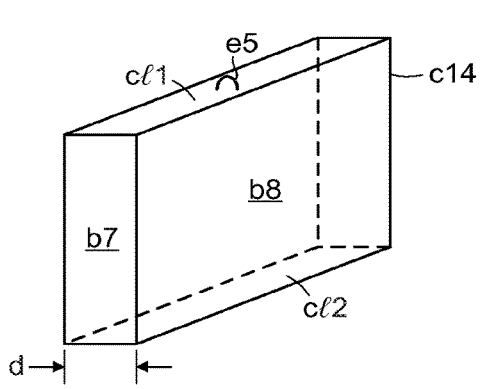
FIGS. 1A-1P are schematic drawings of exemplary caged bags.

For convenience, certain terms employed in the specification, examples and claims are collected here. Unless defined otherwise, all technical and scientific terms used in this disclosure have the same meaning as commonly understood by one of ordinary skill in the art to which this disclosure belongs. The initial definition provided for a group or term provided in this disclosure applies to that group or term throughout the present disclosure individually or as part of another group, unless otherwise indicated.

The compositions of the disclosure can additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

As used herein, "a" and "an" are used to refer to one or more than one (i.e., to at least one) of the grammatical object of the article. By way of example, "an element" means one element or more than one element.

As used herein, "adsorbent" refers to porous particulate material or porous continuous solid-phase material or a nonporous particulate solid phase material which is useful for adsorbing or absorbing substances from liquid or gaseous samples.

As used herein, "bed" refers to a volume of particulate material or of a porous membrane, disc, filter or monolith.

As used herein, "cage" refers to a structure of one or more cage elements that collectively provide or contribute simultaneously to both enclosure and open access (provide or leave openwork) to a material of interest, where the material of interest is a bed or a bag.

As used herein, "cage element" refers to, but is not limited to, a mesh, bar, rod, stick, magnet, wire, spring, cable tie, tie wrap, tagging fastener or barb, clamp, frame, brace, clip, hook, cover, cap, lid, ring, a container, or equivalents thereof.

As used herein, "container" refers to a nonporous vessel such as a test tube, vial or jar.

As used herein, "connected" refers to when a part of a device is attached, held or tied together, by physical or magnetic means to another part of a device such that when one part moves and is connected to a second part, the second part moves.

As used herein, "locked" means prevented from moving in or with respect to another portion of an apparatus such as a cage, even when the cage moves, referring to a part or the whole of a bed or bag.

As used herein, "microporous bag" refers to a bag where the diameter of the pores is selected from values of 1 micron to 1000 microns. A "microporous bag" is also referred to simply as a "bag" unless noted otherwise.

As used herein, "physically" means something accomplished by a solid-to-solid contact. The contact can be accomplished by one or more magnets.

As used herein, "monolith" refers to a continuous solid porous material, analogous to a loaf of bread.

As used herein, "sealed" means closed covalently or physically, including closure by folding.

As used herein, "porous" means filled with holes, referring either to a bed of porous material as a whole (which may comprise nonporous or porous particles), or to an individual component of the bed such as a porous particle that is individually porous.

As used herein, "immobilized" means that porous material is prevented from movement that would cause the disintegration, degradation, or the formation of fines by the porous material.

As used herein, "synthetic" means produced by synthesis, where two or more parts (e.g., atoms, molecules, or components) are brought together to form a new whole. Examples of synthesis include the synthesis of Carboxen or of DEAE-agarose. "Synthesis" does not include production by degradation, even if performed by a person, such as the degradation of natural matter to form a graphitized carbon, graphitic carbon, or charcoal carbon.

"The term "about" is used in this disclosure to mean a value ±20% of a given numerical value. Thus, "about 60" means a value between 60 minus 20% of 60 and 60 plus 20% of 60 (i.e., between 48 and 72").

2. Caged, Bagged Beds

According to aspects of the present disclosure, the usefulness of solid phase porous materials, hereinafter termed "porous materials ", is extended by incorporating them into a caged bag in the form of a bed. The bed can comprise one or more materials, depending on the purpose for which the invention is to be used.

Many types of particulate or nonparticulate materials can be incorporated in the bed, such as silica, metal oxides (e.g. aluminas, zeolites), metals, plastics, carbons (e.g. graphitized carbon, graphitic carbon, charcoal carbon or a synthetic form of carbon such as Carboxen™ carbon), organic polymers (e.g. polysaccharides, polyamides, polyaromatics, polyesters, polyethers). Many kinds of organic or biological groups or substances can be incorporated into the bed covalently or noncovalently such as alkyls, aryls, ionic groups, biomolecules (e.g. proteins, lipids, carbohydrates including polysaccharides, nucleotides, oligonucleotides).

A diversity of affinity and catalytic ligands can be incorporated into the bed. For catalysis, a catalytic substance such as an enzyme, metal, or organometallic substance can be incorporated into the porous material. The bed can also comprise viruses and biological cells (e.g., bacteria, yeast, and animal cells), where the viruses or biological cells are the particles of the bed. In some embodiments, the viruses or cells are attached to another material which acts as a matrix to provide structural integrity to the bed, or to provide further desired properties (e.g., adsorptive, absorptive, catalytic activity, etc.) to the bed. In other embodiments, a material is coated with a substance that allows for specific binding to a target analyte. These materials include, but are not limited to, antigens, antibodies, enzymes, substrates, receptors, and ligands.

Chromatographic particulate packings are widely employed as adsorbents for solid phase extraction. A wide variety of such packings, usually porous, are available from many companies, made from both organic and inorganic adsorbent materials. In certain embodiments, these packings are used in the beds to provide adsorptive capabilities to the bed.

For extraction of small samples, embodiments disclosed herein utilize small bags of adsorbent porous material that can be caged in a small container of the sample in several ways, while permitting access of the sample to the bed of porous material. This permits progressive addition and removal of sample, washing solvent, and elution solvent to the container, making solid phase extraction an exercise in pipetting that can be done manually, but is also readily automated. The caged bag can also be suspended above the sample to provide headspace extraction.

The cage can be a rod or stick having at one end an attached bag of porous material. Options for effecting the attachment that locks at least part of the bag onto the rod or stick include, but are not limited to, a slot, clip or glue. This device makes solid phase extraction an exercise in dipping or stirring that can be manual or automated.

The bag may comprise many varieties of porous cloth or mesh materials selected from plastics (e.g. polyamides such as nylon, polyesters, polyethers, polyalkyls such as polypropylene, polyfluoroorganics), metals (such as stainless steel cloth), proteins and polysaccharides. The bag is preferably made from microporous cloth, but can also be nanoporous (pores in the 10-100 nm range) or milliporous (pores in the 1 to 3 mm range). The bag can have any profile such as square, rectangle, box, ellipse, circle, cylinder, shell, tube, or cone. The bag within its very walls or fabric can contain porous material. An oblong bag is preferred for extraction of a relatively small sample volume, especially where the length (top to bottom) of the bag exceeds the width of the bag in a flattened state by a factor of three or more, but can be a factor of 1.5 or more.

The cage can comprise many kinds of rigid or semi-rigid materials selected from metals (e.g. steel, stainless steel, bronze, brass, aluminum, titanium, gold, tin, lead, zinc, copper, silver, iron, nickel or platinum) glasses, plastics and polysaccharides. The metal can be coated with an organic polymer such as polytetrafluoroethylene. The cage can be inside, within or outside of the bag. The cage is within the bag when it is an integral part of the bag, as by embedding or covalent bonding which may bridge different segments or ends of bag material together to create a bag which is partly porous and partly cage.

The cage preferably extends or contributes to the extension of the adsorbent in the bag by forming or sustaining a bed of adsorbent that is more distributed, more spread out, in the bag, than in the absence of the cage. The cage may also function only by providing a rigid structure to control the motion of the bed in a sample being treated as by connecting the cage that contacts the bag to a motor.

In certain embodiments disclosed herein, a bed of solid phase porous material can be porous in three ways. In the first way, the bed comprises particles that are nonporous, where the porosity of the bed then arises from the space between the particles. In the second way, the bed comprises porous particles, so the porosity arises from the spaces within and between the particles. In the third way, the bed is a continuous, nonparticulate material like a membrane, disc, filter or monolith that is porous.

In certain aspects, the bed further comprise a porous filter, disc, monolith or membrane chromatographic material that is contacted by a cage or caged bag to work as a porous paddle to simultaneously stir and extract a sample with high efficiency.

The cage can comprise one or more clips or clamps, for example of the types used for surgery or dialysis. These clips or clamps may be used either to seal one or more microporous parts of the bag; to hold the sides of a cage together; or to help to flatten and immobilize porous material in the bag.

In some embodiments, the apparatus further comprises a physically-flattened and physically-immobilized bed of solid-phase porous material in a microporous metal bag, especially a metal cloth bag, wherein the said bag provides or contributes to the said flattening and immobilization.

3. Exemplary Embodiments

The following describes exemplary embodiments, as depicted in FIGS. 1-4. Nothing in this section should be interpreted as limiting the scope of the invention.

FIG. 1 is a series of schematic drawings depicting exemplary embodiments of the invention. As used throughout FIG. 1, the letter generally c (structure depicted with a solid or dotted line) designates a cage or cage element, b (structure depicted with dashed lines) designates a bag which contains porous material, l designates a lid component of a cage, f designates a fin, s designates a stem, e designates an eye hook for connection to a motor, and a or x designates an axis of rotation.

FIG. 1A represents a device in which a single cage element c is used to form the cage. In certain embodiments, the cage element also contains an eyehook e for connection to a motor. Eyehooks are commonly used in the art to secure objects to one another. In the embodiments disclosed herein, an eyehook prevents the caged bag from moving independently of the motor shaft. This device can give the user the advantage of forming the last seal on the bag b, after porous material is added, by folding over the bag and securing it on a microporous part with the cage, or doing this without folding, thereby avoiding problematic heat sealing of the last side. In this device, a clamp or clip, for example, could provide the cage. In one embodiment, a relatively stiff wire cloth is used for the bag in this device, giving the advantage that the stiffness of the cloth could work in combination with the cage to extend the porous material in the bag, and thereby facilitate high speed solid phase extraction. The cage could then increase the extension of porous material in the metal bag mechanically by squeezing the microporous part of the bag. Such a squeezed metal bag could also sufficiently immobilize the porous material to allow use of a fragile porous material in the bag. In another embodiment, a soft bag (e.g. soft wire cloth or soft nylon) is employed, and the adsorbent is nonfragile, so that the bed does not need to be extended to provide immobilization of the porous material for the purpose of minimizing formation of fines. In this latter embodiment may be preferred to twist the cage back and forth or move it up and down in a sample with a motor to simultaneously tumble the porous material and force sample liquid through the bag for a rapid extraction or other effect in a controlled way. FIG. 1A also represents a caged monolith for use in this invention, as long as a rigid monolith is employed such as a porous silica monolith, obviating the need for a bag. Nevertheless, a cage or cage and bag can still be used to protect the monolith from fragmentation or exposure to larger insolubles in a sample.

FIG. 1B depicts a device in which the bed of porous material in the bag is sandwiched by the cage, since the cage consists of two cage elements c1 and c2, with a bed of porous material sandwiched in between them. This device has the assembly advantage that a user could start with bag tubing (as a strip or on a roll), cut off to a length of interest to create a bag b1, seal one side with cage element c2, add porous material and seal the other end of the bag with c1. As for device 1A, device 1B can benefit from a wire cloth bag, or by use of a twisting motor, depending on whether a fragile or nonfragile adsorbent is employed in the bag. In another embodiment of device 1B, available in the case of nonfragile porous material, device 1B is spun around axis a parallel to the ground. This could be accomplished by placing the two ends c1' and c2' into a clamp that thereby fixes the relative location of c1 and c2, and then using a motor to rotate device 1B around axis a, or twist device 1B around axis a, thereby simultaneously tumbling and forcing sample liquid or gas through the bag.

FIG. 1C depicts a device in which a clip c3 is employed as the cage to simultaneously extend and sandwich porous material in a bag b2. In this example, the clip is being operated like a paper clip. The options and advantages for the prior devices apply here as well, including the option to provide the last seal on the bag by folding it over and then securing it with the clip. The clip can provide sufficient immobilization of the porous material so that a fragile adsorbent can be used, and the extension of the porous material in the bag by the clip further achieves a flattening to speed up the rate sample treatment by minimizing the path length for flow of liquid through the bag. To set up this device for a particulate porous material the porous material could be extended in the bag by flattening the filled bag with a ruler before the clip is used to lock in the spread of the porous material, and to keep the bed of porous material in a substantially flattened and immobilized condition during a sample treatment process such as solid phase extraction process.

FIG. 1D depicts a device in which the cage consists of three cage elements (c4, c5 and c6), and the porous bed is sandwiched by these cage elements that collectively provide a cage. Cage element c4 also comprises an eyehook e2 for connection to a motor. Cage element c5 (a clip) especially provides extension of the porous material in the bag b3 to achieve the advantages of an extended bed that are pointed out above. In particular, this embodiment combines the advantages of simple sealing of the bag by the user (use of clamps, clips or the like rather than any requirement for heat sealing or sealing by sewing at the site of use), opportunity to employ fragile particles, and flattening of the bed to enhance the rate of sample treatment.

FIG. 1E depicts a device in which the cage comprises two meshes (two cage elements) which sandwich the bag of porous material b4 and keep the bed extended. It is convenient to hold the two cage elements c7 (second element not shown) tightly against the bag, in order to maintain the extension of the bed, by installing a tie wrap tightly at t1 and at t2. Tie wraps are inexpensive and used as disposables. They can be removed at the end of an extraction process with a metal snipping tool. A stiff metal such as stainless steel mesh, or such mesh coated with a polyfluoro organic polymer, is preferred for the two cage elements to substantially extend, flatten and immobilize the bed of porous material inside the bag.

FIG. 1F depicts a device in which the cage comprises five cage elements (c8 to c12) to sandwich and thereby substantially extend, flatten and immobilize the bed b5 of porous material. Cage element c10 also comprises an eyehook e3 for connection to a motor.

FIG. 1G depicts a device in which the cage c13 comprises two frames, each comprising one or more bars, to sandwich and substantially extend the porous material. The cage further comprises an eyehook e4 for connection to a motor. As in device 1E, tie wraps (not shown) can be used to hold the frames together, or they can be fastened together around the bag b6 in another tight way such as by screws or clamps. This embodiment is especially useful for much larger beds of porous material, in which the device is employed for sample treatment such as solid phase extraction at a preparative industrial level, e.g. the device could provide a bed surface of a square meter or more in size. The frames of this embodiment can also have cross bars perpendicular to the bars that are shown to further sandwich and extend the bed of porous material as needed. The frame and bars can be constructed from any rigid materials such as metal, hard plastic, glass or wood.

Figures 1, 1H, 2:
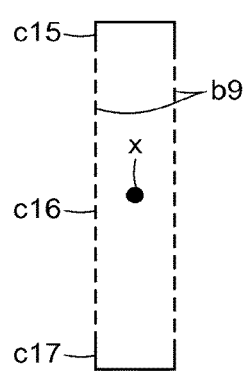
FIG. 2 is a schematic diagram of a motor-connected porous extraction paddle in a jar, where the paddle is connected to the shaft of the motor by a beaded cable tie.

FIG. 1H depicts a device (represented by three drawings, 1H-1, 1H-2, and 1H-3), in which there are three cage elements: frame c14, and two cage lids c11 and c12. This device is intended for reuse, so a wire cloth is preferred for the microporous bag. Cage lid c12 would generally be a permanent bottom. Cage lid c11 would be a removable top. This device, like the embodiment depicted in FIG. 1G, is intended especially for large, industrial scale solid phase extractions. Additional bars can be added to further strengthen the device. Distance d can be fixed in this way, e.g. at a value of 5 millimeters or 2 millimeters, throughout the bed, to provide a uniform extension of the bed. The device depicted in FIG. 1H can be set up in two ways, depending on whether the cage is outside of the bag (as illustrated in FIG. 1H-3, showing bag b11 external to cage c18, which can be rotated about axis x1.), or is within the bag in an integral or embedded way (FIG. 1H-2). In FIG. 1H-2, much of the cage frame, comprising c16 and c17, at least on the larger faces, is made of bag material, and the rest of the frame is bars. The embodiment shown in FIG. 1H-2, due to the significant flattening of the bed, can provide substantial immobilization of the bed by filling up with adsorbent close to the lid, especially considering that stirring the bag b9 of the device depicted in FIG. 1H-2 around axis x would give negligible tumbling at most of the porous material in this bag design. FIG. 1H-2 represents a bag which is partly a cage, so the cage is within the bag in an integral sense.

Figures 1, 1H, 2, 3:
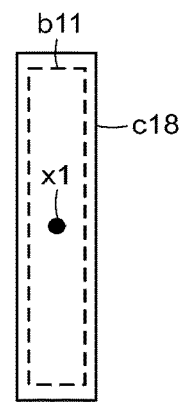
FIG. 3 is a schematic diagram of a motor-connected porous extraction paddle, where the paddle is connected to the shaft of the motor via a bar.
Figures 1, 1I:
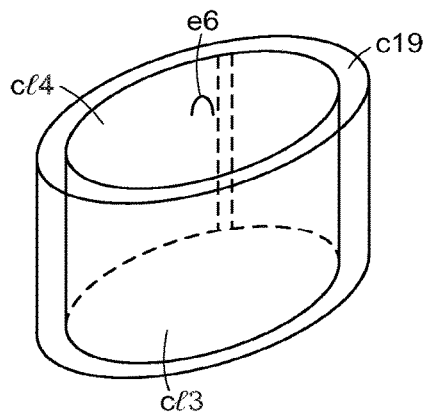
Figures 1, 1I, 2:
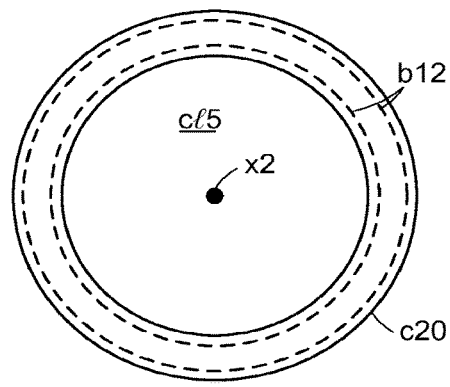

FIG. 1I-1 depicts a side view of a device in which three cage elements are brought together to form a hollow cylinder c19, with cage lid cl3, and cage lid cl4, respectively. Cage lid cl4 also comprises an eyehook e6 for connection to a motor. FIG. 1I-2 depicts a top view of the same device, showing bag b12 supported by cage c20. Cage lid cl5 is also depicted, and an eyehook for connection to a motor (not shown) may be placed at the location of x2, the axis about which the caged bag can be rotated. This device essentially is a wrap-around version of device the device shown in FIG. 1H, and can be constructed and used similarly in two modes, one of which is illustrated in FIG. 1I-2. The cylinder can have a constant or changing radius from top to bottom. In this device, the bed of adsorbent has the shape of a hollow cylinder. In some embodiments, the cylinder is a right circular cylinder and in others it is an elliptic cylinder.

Figures 1, 1J:
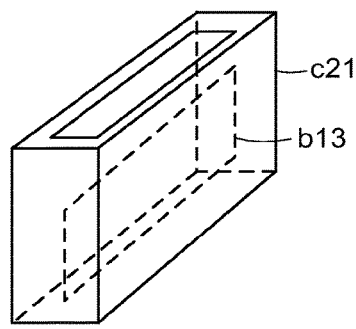
Figures 1, 1J, 2:
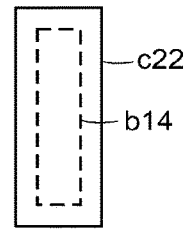
Figure 2:
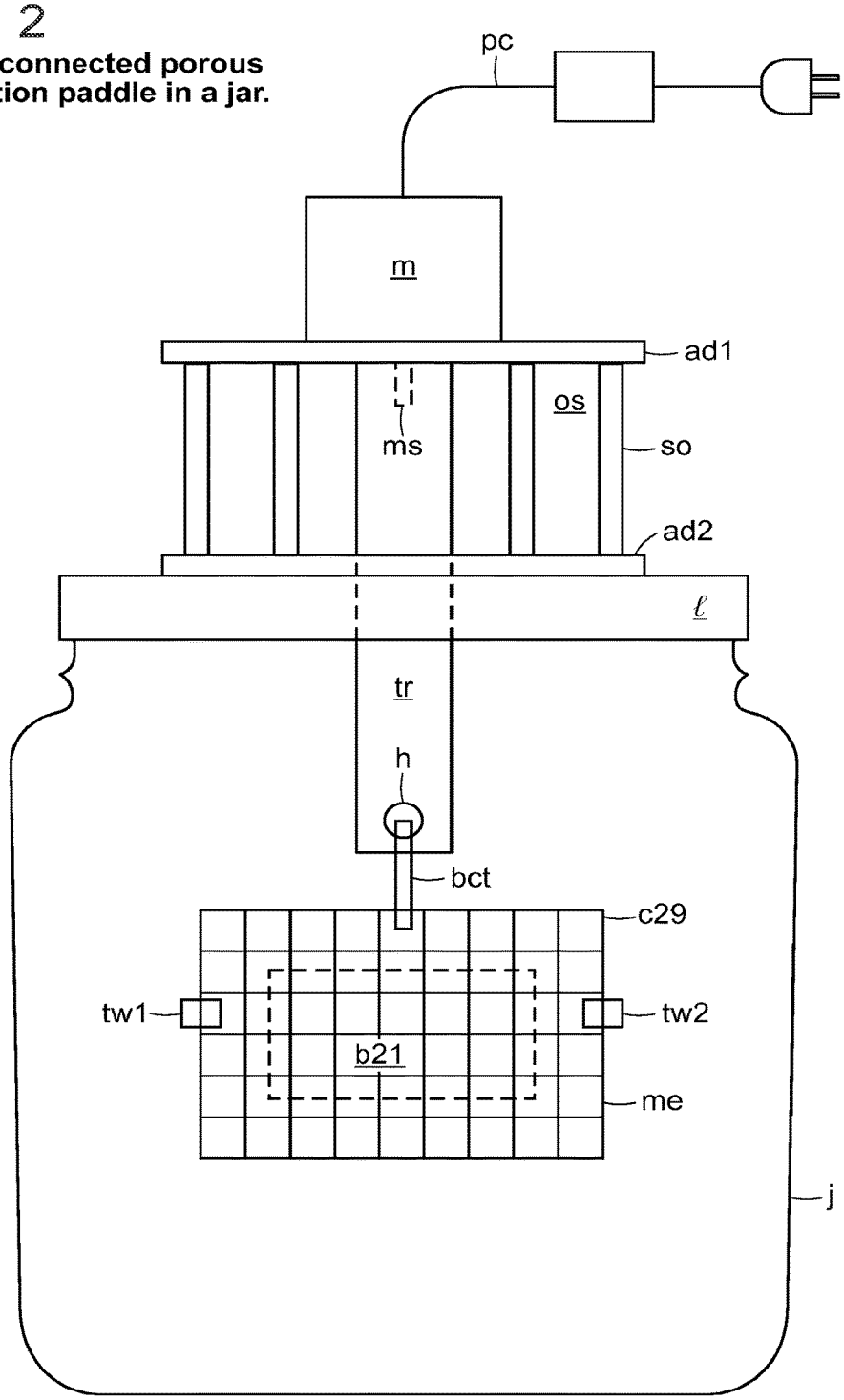
Figure 3:
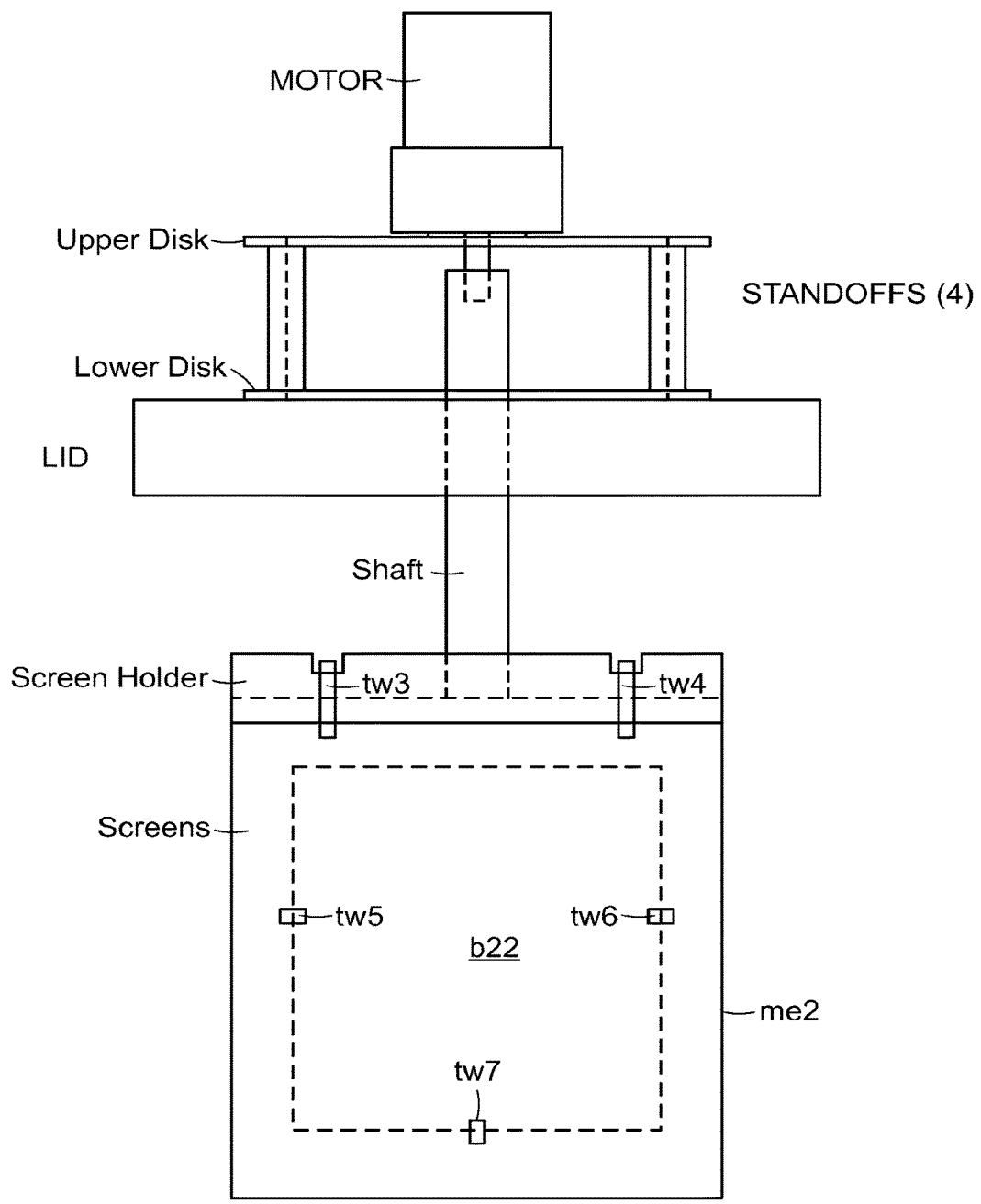

In the device depicted in FIG. 1J (angled view FIG. 1J-1, top view FIG. 1J-2), the cage c21 is a frame having bars on its sides, with a slotted lid (not shown) having the same width of its opening as the inside of the frame. With this device, there is no need to extend the bed in the bag (b3 in FIG. 1J-1 and b14 in FIG. 1J-2) before the bag is placed in the cage. By pulling the bag with particulate material into the inside of the cage through the slot, the porous material is spread in the bag, and the cage substantially locks this extension of the bed into place.

In the device depicted in FIG. 1K, a finned wheel, the device shown in FIG. 1I-2 is modified to contain fins f, so that rotating the device depicted in FIG. 1K clockwise on axis x3 forces more liquid through the bag b15. Devices depicted in FIGS. 1A-1J and also FIGS. 1L-1P can also be modified to have fins (not shown).

In the device depicted in FIG. 1L, multiple bags b16, such as four (illustrated) are each installed in cages c23. In other embodiments, the caged bagged beds can be selected from the devices shown in FIGS. 1A-H and FIG. 1J can be oriented and put together as shown in FIG. 1L. The device of FIG. 1L can also be set up with an integral cage as discussed for FIG. 1H. The device of FIG. 1L can be rotated around axis x4.

FIG. 1M depicts a device comprising bags b17 and cages c24 that is a curled form of FIG. 1L, and can also be operated with an integral cage. This device can be rotated around axis x5. In FIG. 1N, the bags b18 are set up at two ends of a cage c25. This device can be rotated around axis point x6.

FIG. 1O shows a curved bag b19 and cage c26, which can be rotated around axis point x7. FIG. 1P has four stems s as part of the cage. Bags b20 in cages c27 can be attached to the stems which are attached to cage element c28. This device can be rotated around axis point x8.

The devices shown in FIGS. 1N, 1O and 1P can also be operated as integral bags. Related designs can be set up to provide the invention. In all of the devices depicted in FIG. 1, magnets or ferromagnets can be used as additional or alternative cage elements.

4. Motor-Connected, Caged, Bagged Beds of Porous Materials

FIG. 2 shows a schematic drawing of a motor-connected, caged, bagged bed in a 0.5 gallon jar that was constructed from the materials listed in Table 1, plus some other materials about to be described. A 0.5 gallon jar j with PTFE-lined lid, 1, (#2000MJ-AS) was acquired from Industrial Glassware and a hole (0.375 inch) was drilled in the middle of the lid. A 0.154 inch hole, h, was drilled to a depth of 0.5 inch into the upper end of a Teflon rod tr (diameter 0.375 inch, Table 1) and a 0.098 inch hole was drilled through the side of the other end of this rod, 0.3 inch from the end. A 12 V DC Gearmotor, m, (#249480) form Jameco Electronics, having a motor shaft, ms, 8 mm (Table 1) was attached with screws to an acrylic disc, ad, (Table 1). This disc was attached to a second acrylic disc, ad2, via four 1 inch standoffs, so, using screws, with open space, os, between the standoffs. The upper end of the Teflon rod was press fitted onto the motor shaft. The overall assembly (Paddle Assembly) was mounted onto the top of the lid, l, via Velcro pads, which put the Teflon shaft through the lid.

A nylon bag, 1.5 inches square, made from nylon woven mesh (WN0025, 25 micron pore) from Industrial Netting, and containing 0.5 gram of porous-silica-based cation exchanger (DSC-SCX, Supelco Sigma-Aldrich), was formed by sealing two nylon squares on three sides with a Medical Grade Sealer (model 540, Accu-Seal Corporation, adding the cation exchanger, and heat sealing the last side of the bag. Sealing conditions: sealing temperature 470 F, dwell time 3 seconds, release temperature 180 F, pressure 80 psi. The cation exchanger was extended (spread) in the bag, after wetting with water, with a ruler; the bag b21 was placed between two squares (2.25×2.25 inches) of stainless steel mesh (Table 1); and the bag was tightly sandwiched between two meshes me using two Ty-Wraps, tw1 and tw2, (Table 1), which substantially immobilized the adsorbent in the bag. The resulting stainless steel cage, containing the bag of adsorbent was attached to the lower end of the Teflon rod with a Beaded Cable Tie (Ty), bct, (Table 1). The motor, m, was plugged into a power cord, pc, consisting of a power supply (Table 1) and a six foot cable with jack (Table 1). In a second Paddle Assembly, TEFZEL Cable Ties, T-TEF-ZEL-04 (Tiewraps.com Inc) replaced the prior nylon ties. When the power cord was plugged into an electrical outlet, the caged bag of adsorbent rotated.

FIG. 3 shows a schematic drawing of a motor-connected, caged, bagged bed for use in a 0.5 gallon jar, similar to that in FIG. 2, except for a faster motor, different mounting of the motor to the lid or the jar, different connections of the shaft to the cage, and a larger bag and cage. Advantageously, the given cage can fully lock in a bag, and fully immobilize (prevent flow) of porous material inside the bag even for different amounts of porous material at least within the range of 0.5 to 3.0 g. The device in FIG. 3 was constructed from the components listed in Table 2. The features and construction of this device are as follows, where the term "screen" refers to a meshed cage element.

In the tested Example, the motor of FIG. 3 was powered by a 9 Volt DC power supply (Item 1). The pigtail, (Item 2), was soldered to the terminals on the motor (Item 3). The Upper Disk was made from a cast acrylic circle (Item 4). Through holes have been drilled for the shaft mount bevel, the 2 motor mount screws (Item 8), and the 4, 1" standoffs, (Item 5). The Lower Disk was made from a cast acrylic circle (item 4). Through holes have been drilled for the 4 standoffs and 1 hole at the center for the shaft to pass through. The Upper Disk was connected to the Lower Disk using the standoffs with nylon flathead screws (Item 7), and nylon hex nuts (Item 6). The shaft was made from Teflon Rod (Item 9). The Teflon rod was cut to length and both ends faced off on the lathe. A lathe was used to center drill a hole in one end of a diameter that allowed a press fit to the motor shaft. The lid has a hole drilled at the center for the shaft to pass through. The complete assembly of the disks with the motor attached was secured to the lid with Sealant (Item 12). The Screen Holder (cage holder) is made from Teflon Bar (Item 13) cut to length. A hole has been drilled in the top side center to allow the shaft a press fit. 2 grooves have been milled to a width and depth to secure a tie wrap. A groove was milled into the bottom to allow for a snug fit of the screen.

The screen was cut from 2 pieces of stainless steel mesh (Item 10) using a metal shears in a size of 3.25×3.65 inches. The screen met was attached to the screen holder using Teflon Tie (Ty) Wraps tw3 and tw4. (Item 11).

The device was assembled with a 2.75×2.75 inch bag b22 sandwiched in the screen that was in turn mounted into the groove of the Teflon bar with Teflon Ties tw5 and tw6, where the bag contained 3.0 g of porous adsorbent material.

5. Small Caged Bags of Porous Materials

FIG. 4 illustrates some examples of small, caged bags, preferably with internal widths in the flattened state of less than 5 mm, containing porous materials in small containers to provide treatments such as solid phase extraction of small samples such as 1-5 ml. While, in principle, a small bag can be stirred or dipped in a small sample via a cage such as a bar, rod or stick manually or via a motor, a small sample container makes it convenient to speed up extraction as needed by simply placing the container with sample and bagged, porous material in it on a shaker, where the bag is at least partly locked in contact with a cage, which cage may comprise the container. Actually, many samples can be treated in parallel in this way. Throughout the figure the bag is represented by a dashed line. The bag mostly is viewed on its side where the part containing the bed of porous material m is illustrated as a loop of the dashed line bag. In FIG. 4A, cage c30 is provided by the cap cp on the container cr in which liquid sample is contained, where sls is the surface of the liquid sample. The bag b23 is seen to be folded over the lip of the container and locked into place there by the cap. A hole h2 is present in the cap for convenient dispensing (pipetting) in and out of sample, washing, and elution solvents. In FIG. 4B, a container cr1 is shown, containing liquid sample ls1. The bag b24 is shown suspended below the surface of the liquid sls1 in the liquid sample by cage element c31 which is an O-ring that functions as a cage, and in preferred embodiments, a polyfluoroorganic O-ring. The bed of porous material pm1 is thereby suspended in the liquid sample. FIG. 4C shows a variation of the configuration shown in FIG. 4B. In FIG. 4C, a container cr2 contains a liquid sample ls2. The bag b25 containing the bed of porous material pmt, is held under the surface of the liquid sls2 by cage element c32, which is also an O-ring that functions as a cage and in preferred embodiments, a polyfluoroorganic O-ring.

Figure 4A:
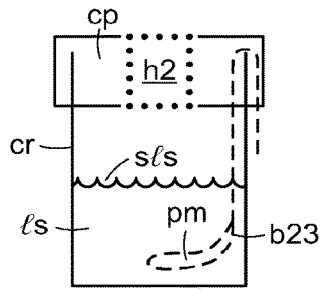
FIGS. 4A-4I illustrate examples of bags containing porous materials caged in a glass or plastic tube.
Figure 4B:
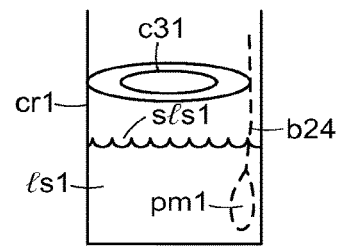
Figure 4C:
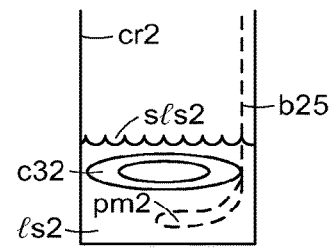
Figure 4D:
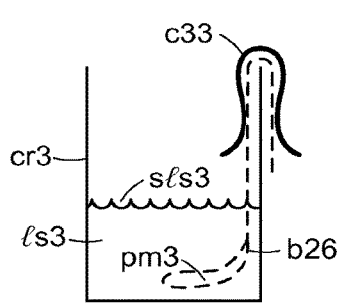
Figure 4E:
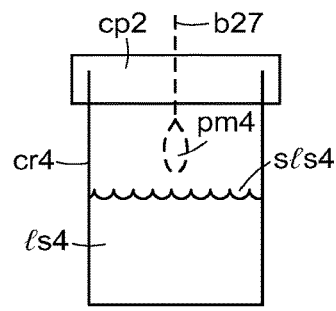

FIG. 4D shows a container cr3 containing a liquid sample ls3 which has a surface sls3. In this embodiment, the bag b26 containing the bed of porous material pm3 is immobilized with a clip c33 functioning as a cage. FIG. 4E shows a container cr4 containing a liquid sample ls4 which has a surface sls4. In this case the bed of porous material pm4 in the bag b27 is suspended above the sample by pulling the bag through a hole (not shown) cap cp2. In this embodiment, the cap is the cage. In this case the bed in the bag is suspended above the sample in order to conduct a head space extraction.

Figure 4F:
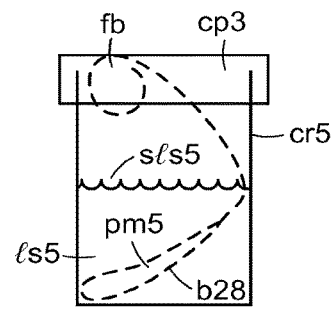
Figure 4G:
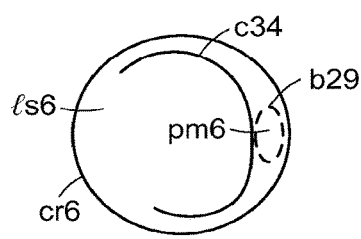

FIG. 4F shows a container cr5 containing a liquid sample ls5 which has a surface sls5. Here, the cage is the combination of the cap cp3 and the container cr5 that lock the bag b28 containing porous material pm5, under tension, in the container, where fb is folded bag. FIG. 4G depicts a top view of a container cr6 containing a liquid sample ls6 where the bag b29 containing porous material pm6 is locked against the wall of the container by the cage c34, which can be something such as, but not limited to a mesh, wire, or spring that is under tension.

Figure 4H:
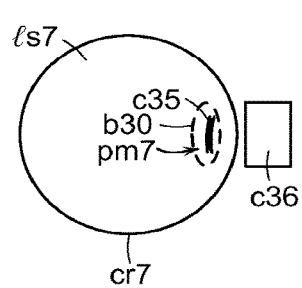

FIG. 4H depicts a top view of a container cr7 containing a liquid sample ls7 where the bag b30 containing porous material pm7 is locked against the wall of the container by the cage c35, which is a ferromagnetic or magnetic bar or wire mounted inside the bag (as shown) or outside of the bag (not shown) in combination with the container as a second part of the cage, and a magnetic field, provided by a magnet or electromagnet c36, as a third part of the cage that locks the bag against the side of the container wall via magnetic force.

Figure 4I:
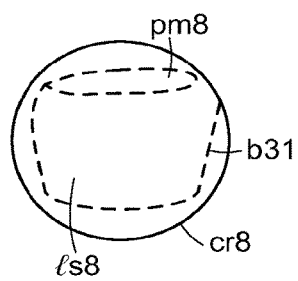

In FIG. 4I, container cr8, containing liquid sample ls8 functions as a cage since the bag b31 containing porous material pm8, is locked by wedging it into the bottom of the container. As in FIGS. 4A-4D, the configurations shown in FIGS. 4G, 4H and 4I enable solid phase extraction or other sample treatments by automatable pipetting steps. In all of these devices, a part of the bag, preferably a microporous part, is under mechanical stress due to the cage in a way and degree that locks this part of the bag in contact with a cage. In all of the depictions of FIG. 4 except for FIG. 4E, the contact of the bag with the container may be more extensive than what is drawn.

6. Advantages and Significance

The apparatuses and methods disclosed herein have several advantages over the prior art. The rate of extraction is high because the narrow bed allows liquid to flow through the bed easily, and a large area for the narrow bed can be set up. The physical immobilization that can be provided of a particulate bed can prevent or limit tumbling of the particulates, thereby minimizing the generation of interfering or unsafe fines from fragmentation of the particulates. Fines can compromise the performance of solid phase extraction, in part by slowing flow through a bed of adsorbent, and may be toxic. The most widely-employed chromatographic packings for solid phase extractions are irregular silica-based materials because they combine low cost with good performance. However, when tumbled, these particulates readily fragment to form smaller particles called fines. The present invention overcomes this problem by immobilizing the bed. Moving the bed as paddle can whisk larger interfering sample insolubles (larger than the pores of the bag) away from the surface of the bag, minimizing problems with clogging. There can also be tangential or turbulent flow at the bag-sample or porous material-sample interface to further reduce clogging. Due to the cage, it is practical to scale up the device even for preparative applications in the pharmaceutical, food, and other industries to isolate valuable target substances, to remove undesired contaminants, or to conduct catalysis, for example. At all scales the device is economical relative to a column form of solid phase extraction since it avoids costs for chromatographic hardware (columns, pumps, tubing, fittings, connectors, valves, and frits); costs for assembly of this hardware; and costs to operate this hardware including flow control.

By promoting the extraction of large sample volumes, and thereby building up a larger quantity of analytes for analysis from a given kind of sample, our invention makes it easier to have a sample analyzed in different ways (by taking aliquots of the sample-exposed adsorbent), and to be able to repeat analyses at later dates for a given sample. This is very important in providing accurate analyses, confirmed analyses, and comprehensive analyses.

The disclosed apparatuses and compositions will lead to a new kind of cohort sample for epidemiology studies. Because of the scaled-up collection of urinary substituents possible from an individual by the use of the claimed devices, a small portion of the urine-exposed adsorbent is adequate for many analytical procedures. The remainder of the analyte-coated adsorbent can be stored for other tests in future years. Further, the changes in a given person's urinary profile can be detected by comparing the analytes in a future urine-exposed adsorbent to the ones in the original sample. This helps to cope with individual variations that can mask detection of disease processes.

The presently disclosed apparatuses and compositions allow for some 24-hour urine collections. These collections currently require the patient to haul a large bottle of her or his urine to the hospital for chemical analysis. With our invention, a patient can instead bring or mail a small extraction bag to the hospital after conducting the urine collection and extraction with a kit in the home.

Ordinarily an extraction bag needs to be made by first forming three seals, as by sewing or heat sealing, filling with adsorbent, and heat sealing or sewing the last side. Unfortunately, the last step can be awkward and it can be difficult to get a proper seal that does not allow the contents of the bag to leak out over time. With the cage technique, the last side of the bag can easily be sealed physically by the cage. The disclosed devices also comprise a cage sealing two or more microporous sides of the adsorbent-containing bag, so that the adsorbent is sandwiched in this way by the cage.

Furthermore, the disclosed apparatuses and methods allow for solid phase extraction that is as easy as dialysis. This can be performed using a tube roll of the disclosed bed and performing the following or similar sequence of steps: cut a segment of a microporous tubing (as from a roll of such tubing), seal one end with a dialysis clip, add adsorbent, seal the other end of the tube segment with a second clip, flatten the adsorbent in the bag via handling, immobilize the adsorbent with a cage, hang the cage onto the end of a motor-connected shaft, lower the shaft-cage-bag assembly into a liquid sample of interest, and plug in the motor to stir the caged bag of adsorbent in the sample.

The disclosed compositions, apparatuses, and methods provide solid phase extraction with multiple adsorbents simultaneously either by mixing adsorbents into a given porous bag, or by exposing a sample to more than one bag at the same time, where each bag contains a different adsorbent or different mixture of adsorbents. There is increasing interest in measuring multiple analytes at the same time in a sample. The scientist currently has the choices of (1) buying different solid phase extraction columns and then using a series of them (which is time-consuming and expensive); (2) buying different bulk adsorbents and preparing one or more columns, such as one containing a mixture of adsorbents (but then column hardware is needed along with skill to prepare a good column); or (3) selecting a commercially-available column that is a compromise in its ability to extract all of the analytes of interest simultaneously (but this compromises the performance of the solid phase extraction).

The disclosed beds, apparatuses, and methods can be used to provide electrolysis or a combination of electrolysis and extraction. In certain embodiments, this is accomplished by using a metal cage or metal bed as an electrode. The electrolysis-extraction process, where the porous material is an adsorbent, would be useful in some cases to remove undesired substances (including their electrolytic decomposition products) from a sample, or to form (electrolytically) and extract a desired target substance. Instead of an adsorbent in the bag, a metal material (e.g. as particles, fibers, wires, sheet) could be placed in the bag and set up as a second electrode via a wire, to provide a stirred electrolysis. Both of the connecting wires to a power supply could be fed up through a hollow stirring shaft. Using a bed as the counter electrode for a cage, which is possible when an insulating bag is employed to avoid contact of the cage and the adsorbent, gives the advantages of having two electrodes in very close proximity, which in turn can provide a relatively constant pH, and a rapid electrolysis due to the stirring and large area of the electrodes.

In certain embodiments, the apparatuses and compositions encompass embodiments that are important for solid phase extraction of gaseous samples, including the use of solid phase materials that have an adsorbed liquid coating to provide absorption of targeted substances from the gaseous samples. Use of a moving paddle can speed up extraction relative to the use of passive air samplers.

In certain embodiments, the disclosed compositions and apparatuses are used in water purification systems. Known devices for purification of water by the consumer, such as the Brita, have the following disadvantages: (1) water is exposed to plastic; (2) the plastic purification cartridges are expensive; (3) the devices are not a green technology since they yield excessive environmental contamination (used plastic cartridges); (4) the limited contact time of the water with the adsorbents in the plastic cartridges limits the degree of purification; and (5) steps are required to set up and wash out fines from the cartridges before use. In contrast, the presently disclosed device can provide in situ purification of water in a glass container in a much greener, simpler and inexpensive way, especially by employing a porous paper bag filled with granular charcoal.

The present apparatuses and compositions are useful for purification of chemical reagents in the laboratory, such as organic solvents, organic solutions, water, and buffers. Purification of these reagents in an in situ way (the reagents are purified in their own container) with our invention will be simple, economical, and minimize exposure to contamination by the environment.

The presently disclosed apparatuses and compositions can be advantageously effective for solid phase extraction of small samples (e.g. 1-10 ml). For this purpose, an oblong bag can be set up and which contains one or more types of adsorbent or absorbent particles. A great variety of such particles is available, and they simultaneously provide speed and high sensitivity for solid phase extraction, unlike the adsorptive coatings of solid phase microextraction and stir bar extraction. This is because the usual chromatographic particles are highly porous, providing lots of capacity even with a thin adsorptive coating.

7. Examples

Example 1

Solid phase extraction with a porous extraction paddle was accomplished by obtaining nylon mesh from Industrial Netting, cutting out two segments (each 49×61 mm) with a scissors, heat-sealing three sides with a medical sealer from AccuSeal, adding 2 grams of Amberlite XAD-4 adsorbent (Sigma CAS 37380-42-0), heat-sealing the remaining side of the bag, spreading the adsorbent evenly in the bag manually, sandwiching the bag between two stainless steel meshes with Ty-Wraps as illustrated schematically in FIG. 2, stirring the caged-bag in 0.5 gallon of an aqueous, visibly-blue solution of bromophenol blue by plugging in the motor, and observing visibly that the adsorbent turned blue as the solution became colorless.

Example 2

Solid phase extraction with a porous extraction paddle was accomplished similarly as in Example 1, but using a different dye and adsorbent. Silica-SCX (0.5 g from Supelco-Sigma) was the adsorbent in the bag, the dye was 1.0 mg of Malachite Green, and the solvent was 0.5 gallon of 0.4% aqueous acetic acid (pH 3). After stirring overnight using the device of FIG. 2, only 7% of the green color remained in the liquid, based on an absorbance measurement at 619 nm, and the adsorbent became colored. In this paddle, the longest length of the bed according to the definition in claim 1 was 60 mm (diagonal through the bed), and the minimum width of the bed according to claim 1 (a calculated distance perpendicular to the bed) was about 0.6 mm, so the ratio of the maximum width to the minimum width according to the definitions in claim 1 was about 100. The same result was achieved by sealing the last side of a bag by folding it down and using the cage to secure the seal. The extraction time was reduced to less than two hours using the device of FIG. 3.

Example 3

Solid phase extraction with a porous extraction paddle was accomplished by forming a nylon mesh bag with adsorbent the same as in Example 1 but with a much smaller size (3.5×40 mm outer dimensions including the fins from the sealing; 2.5×40 mm for inner bag aside from the fins). Silica-SCX (15 mg from Supeco-Sigma) was the adsorbent in the bag, and the dye was 5 ug of Malachite Green (MG) in 1.5 ml of 0.4% aqueous acetic acid (pH 3). The bag was locked in a capped 2.0 ml vial according to the configuration shown in FIG. 4F. After shaking the vial at room temperature for 2 hr, 8% of MG remained in the liquid, based on an absorbance measurement at 619 nm, and the adsorbent became colored.

Table 1 provides exemplary hardware that can be used to build the porous extraction paddle system of FIG. 2 along with a motor and shaft to rotate the paddle in the sample. Nothing in this table should be interpreted to limit the scope of materials that may be used to build other embodiments of the claimed invention. In light of the instant disclosure, one of skill in the art would be able to envision a variety of materials and configuration that would remain within the scope of the claimed invention.

TABLE 1

Materials to build an apparatus that conducts solid phase extraction with a porous extraction paddle.

| Description | Supplier | Supplier Part No. | Needed Per Setup |
|---|---|---|---|
| Power Supply, DC, 15 Volt, 1 Amp | Jameco Electronics | 1940521 | 1 |
| 6' cable with Jack, 2.1 MM × 5.5 MM | Jameco Electronics | 2114600 | 1 |
| Motor, 12 V DC | Jameco Electronics | 249480 | 1 |
| Machine Screw, Nylon, Flat Head, 6-32 Thread, ½" Length | Small Parts, Inc | B000FN5QAG | 4 |
| Standoff, Nylon Male-Female, 1", 6-32 Thread | Small Parts, Inc | B00137PA61 | 4 |
| Hex Nut, Nylon, 6-32 Thread | Small Parts, Inc | B000FMU8R1 | 4 |
| Mesh, Stainless Steel, 8 × 8 grid | Small Parts, Inc | B001CTWZGK | 5" × 2.5" Piece |
| Machine Screw, Stainless Steel, Metric 2.5, 6 MM Length | McMaster-Carr | 91801A135 | 2 |
| Teflon Rod, ⅜" Diameter, 12" L | McMaster-Carr | 8546K12 | 4" |
| Clear Cast Acrylic Circle ⅛" Thick, 3" Diameter | McMaster Carr | 1221T15 | 2 |
| Beaded Cable Tie, Nylon, 4" | MSC Industrial | 62542865 | 1 |
| Ty-Wrap, Nylon, 3.62" × .091" | MSC Industrial | 54065842 | 2 |

Table 2 provides exemplary hardware that can be used to build the porous paddle extraction system of FIG. 3, which has high speed stirring capability.

TABLE 2

Materials to build the apparatus of FIG. 3, which conducts solid phase extraction with a porous extraction paddle.

| Item No. | Description | Supplier | Part No. | Per Setup |
|---|---|---|---|---|
| 1 | AC/DC Power Supply 9 Volts | Jameco Electronics | 1940686 | 1 |
| 2 | JACK, 2.1 M × 5.5 × 12 MM, 6 FT PIGTAIL | Jameco Electronics | 2114600 | 1 |
| 3 | MOTOR GEAR, 12 VDC, 156 MA | Jameco Electronics | 162191 | 1 |
| 4 | Clear Cast Acrylic Circle, 3" Diameter, ⅛" thick | McMaster-Carr | 1221T15 | 2 |
| 5 | Nylon 6/6 Male-Female Standoff 6-32 1" L | Small Parts, Inc. | B00137PA6I | 4 |
| 6 | Nylon 6/6 Hex Nut, #6-32 | Small Parts, Inc. | B000FMU8RI | 4 |
| 7 | Nylon Screw, Flat Head, #6-32, ½" L | Small Parts, Inc. | B000FN5QAG | 4 |
| 8 | SS Screw, Flat Head, M2.5, 6 MM L | McMaster-Carr | 91801A135 | 2 |
| 9 | Rod Made of Teflon ® PTFE ⅜" Diameter | McMaster-Carr | 8546K12 | .27 ft. |
| 10 | Mesh, Stainless Steel 8 × 8, .025 Diameter | McMaster-Carr | 9238T58 | 3.25" × 3.5" |
| 11 | Tie Wrap, Dupont Tefzel, 4" L × .094 W | Tiewraps.com | T-TEFZEL-04 | 5 |

TABLE 2-continued

Materials to build the apparatus of FIG. 3, which conducts solid phase extraction with a porous extraction paddle.

| Item No. | Description | Supplier | Part No. | Per Setup |
|---|---|---|---|---|
| 12 | Dow Corning 732 Silicone Adhesive/Sealant, Clear | McMaster-Carr | 7587A37 | — |
| 13 | Bar, Teflon, PTFE, ½" × ½" × 12" | McMaster-Carr | 8735K36 | .3 ft. |

The invention claimed is:

1. A system for extracting a substance of interest out of a liquid to form an extracted liquid and an isolated substance of interest, comprising:
   a. porous extraction material;
   b. a porous bag adapted to load and enclose the porous extraction material;
   c. a substantially rigid cage having at least two sections that sandwich and squeeze the loaded porous bag from both sides and immobilize the loaded porous bag relative to the rigid cage, yielding a rigid caged bag having substantially uniform thickness, and having a length and width being substantially larger than its greatest thickness;
   d. a mechanism coupled to the caged bag adapted to move the liquid through the caged bag to efficiently collect the substance of interest resulting in the extracted liquid and the isolated substance of interest.

2. A system for efficiently extracting a substance of interest out of a liquid to form an extracted liquid and an isolated substance of interest, comprising:
   a. porous extraction material;
   b. a porous bag adapted to receive and load the porous extraction material;
   c. a substantially rigid cage having at least two sections that sandwich, squeeze and immobilize the loaded porous bag from both sides relative to the rigid cage, yielding a rigid caged bag having substantially uniform thickness, and having a length and width being substantially larger than its greatest thickness;
   d. a stirring actuator adapted to move the liquid through the rigid caged bag to efficiently collect the substance of interest, resulting in the extracted liquid and the isolated substance of interest.

3. A caged bag for extracting a substance of interest out of a liquid, comprising:
   a. a porous bag enclosing a porous extraction material adapted to extract substances from liquids passing through it;
   b. a substantially rigid cage that is adapted to open to receive and then close upon the porous bag with its porous extraction material; wherein the rigid cage sandwiches and squeezes the bag from both sides, yielding a rigid filled bag having substantially uniform thickness, the rigid cage also having a length or width at least two-fold greater than its greatest thickness, and the porous bag filled with porous extraction material is adapted to extract substances from liquids passing through it.

4. The caged bag of claim 3, wherein the porous bag is constructed of a material being at least one of the group consisting of:
   polyamide, polyester, polyalkyl, polysaccharide, and metal material.

5. The caged bag of claim 3, wherein the rigid cage is adapted to be easily opened and closed allowing the porous bag and extraction material to be removed and replaced.

6. The caged bag of claim 3 wherein the ratio of said length to said thickness of the bed is at least 5.

7. The caged bag of claim 3, wherein at least 90% of the volume of the porous bag in the rigid cage is occupied by said porous extraction material.

8. The caged bag of claim 3, wherein the porous bag is comprised of:
   porous meshed cloth having pores in the range of about 1 micron to about 100 microns.

9. The caged bag of claim 3, wherein the porous bag further comprises:
   a loading opening.

10. The system of claim 3, wherein the porous extraction material comprises one of the group consisting of: particles, a porous monolith, a porous disc, a porous membrane and a porous filter.

11. The system of claim 3, wherein the rigid cage comprises at least one of:
   mesh, clamp, frame, brace, clip, and hook.

12. The system of claim 1, wherein the porous extraction material is coated with a substance that binds to a target substance to be extracted.

13. The system of claim 2, wherein the porous extraction material is one of the group consisting of: carbon, vinyl polymer, and silica.

14. The system of claim 1, wherein the porous extraction material consists of particles having a size distribution with greater than 50% of the particles having a diameter within the range of 5 µm to 100 µm.

15. The system of claim 1, wherein the mechanism moves the liquid through the caged bag by stirring, shaking or rotating the caged bag.

16. The caged bag of claim 3, wherein the bag has a length and width at least ten-fold larger than its greatest thickness.

17. The caged bag of claim 3 in which the rigid filled bag is adapted to receive the liquid equally to either side.

18. The caged bag of claim 3, wherein the porous extraction material is one of the group comprising: carbon, vinyl polymer, and silica.

19. The caged bag of claim 3, wherein the porous extraction material consists of particles having a size distribution with greater than 50% of the particles having a diameter within the range of 5 µm to 100 µm.

20. The system of claim 1, wherein the mechanism is an actuator coupled to the caged bag adapted to move the caged bag through the same liquid repeatedly from one side of the bag to the other.

21. The system of claim 1, wherein the mechanism employs gravity to move the liquid through the caged bag.

* * * * *